United States Patent [19]

Ninomiya et al.

[11] 4,312,733
[45] Jan. 26, 1982

[54] UNIT FOR MEASURING ALKALI METAL VAPOR CONCENTRATION

[75] Inventors: Susumu Ninomiya; Fumio Ohtsuka; Hiromichi Nei, all of Yokohama; Mituo Harata, Kawasaki; Osamu Takikawa, Chigasaki; Atsuo Imai, Yokohama, all of Japan

[73] Assignee: Tokyo Shibaura Denki Kabushiki Kaisha, Kawasaki, Japan

[21] Appl. No.: 73,134

[22] Filed: Sep. 6, 1979

[30] Foreign Application Priority Data

Sep. 25, 1978 [JP] Japan .................. 53-116687

[51] Int. Cl.³ ........................... G01N 27/58
[52] U.S. Cl. .................. 204/195 S; 204/1 T
[58] Field of Search ........... 204/1 S, 195 S, 195 R, 204/1 A

[56] References Cited

U.S. PATENT DOCUMENTS

| | | | |
|---|---|---|---|
| 1,601,383 | 9/1926 | Todd | 204/195 R |
| 3,558,280 | 1/1971 | Panson et al. | 204/195 S |
| 3,616,272 | 10/1971 | Goerg et al. | 204/195 R |
| 3,698,384 | 10/1972 | Jones | 204/195 S |
| 3,767,469 | 10/1973 | Flais et al. | 204/195 S |
| 3,819,499 | 6/1974 | Hoogeveen et al. | 204/195 S |
| 3,958,937 | 5/1976 | Shibata et al. | 204/195 S |
| 3,960,500 | 6/1976 | Ross et al. | 204/1 S |
| 3,962,866 | 6/1976 | Neidhard et al. | 204/195 S |
| 4,098,650 | 7/1978 | Sayles | 204/195 S |
| 4,129,491 | 12/1978 | Obiaya | 204/195 S |
| 4,166,009 | 8/1979 | Fray | 204/195 S |

FOREIGN PATENT DOCUMENTS 49-7198 2/1974 Japan.
50-52493 5/1975 Japan.

OTHER PUBLICATIONS

Thompson, "Vapor Traps Protect Liquid Metal Systems", Power Reactor Technology, vol. 8, No. 4, Fall 1965, pp. 259-270.
Weber, "Energy Conversion", vol. 14, pp. 1-8, 1974.

Primary Examiner—G. L. Kaplan
Attorney, Agent, or Firm—Oblon, Fisher, Spivak, McClelland & Maier

[57] ABSTRACT

A unit for measuring the alkali metal vapor concentration of a gaseous phase, comprising
  a gas inlet pipe,
  a container provided with a heating means for vaporizing the alkali metal mist contained in the gas, and a β-alumina sensor serving to measure the alkali metal vapor concentration,
  a vapor trap connected to the container via a gas conduit and serving to condense and remove the alkali metal vapor contained in the gas,
  a gas pump having the suction port connected to the vapor trap via a gas conduit, and
  a gas discharge pipe connected to the discharge port of the gas pump.

The unit can be mounted anywhere and is easy to handle and operate.

7 Claims, 2 Drawing Figures

UNIT FOR MEASURING ALKALI METAL VAPOR CONCENTRATION

BACKGROUND OF THE INVENTION

This invention relates to a unit for measuring the alkali metal vapor concentration of a gaseous phase, particularly, a unit suitable for measuring the sodium vapor concentration of the gas serving to cover a liquefied metal sodium or the like used as a coolant or heating medium in, for example, a fast breeder.

A liquefied metal is used as a coolant or heating medium in various industrial facilities including a fast breeder. It is customary to use alkali metals like sodium, potassium and alloys thereof as the coolant or heating medium. In some cases, it is necessary to measure the alkali metal concentration of the gas like Ar gas serving to cover the liquefied alkali metal because, if the alkali metal concentration of the cover gas is unduly high, the alkali metal tends to deposit on the piping of the cover gas, thereby causing plugging or corrosion of the cover gas piping. The measurement of alkali metal concentration is also required in some other industrial or laboratory devices handling alkali metals for the purpose of, for example, monitoring the leakage of alkali metal vapor. Among the alkali metals, sodium is most frequently used in the liquedfied form and it is of high importance in many cases to measure the sodium vapor contration.

The prior arts for measuring the sodium vapor concentration include, for example, a sampling method in which a sample gas containing sodium vapor is taken from a sodium vapor system and subjected to a quantitative analysis. However, the sampling method is not satisfactory in that it is impossible to measure continuously the sodium vapor concentration of the gas.

An electric discharge method is also known to the art, which utilizes the fact that the electric discharge initiation voltage between a pair of flat electrodes disposed in parallel in a gas which contains sodium vapor depends on the sodium concentration of the gas. In this method, however, not only the sodium vapor concentration but also the particle size and particle number density of the sodium mist accompanying the sodium vapor provide the parameters of the measured value, resulting in that the pulse signal generated by the discharge fails to reflect accurately the total sodium concentration, i.e., the sum of the sodium vapor and sodium mist. In other words, the conventional electric discharge method is not satisfactory in reliability of the measured value.

As a device capable of overcoming the drawbacks described above and of detecting the sodium vapor concentration at a high accuracy, Japanese Patent publication No. 49-7198/1974 discloses a sodium vapor sensor utilizing a $\beta$-alumina porcelain as the electrolyte. The sodium vapor sensor consists essentially of a $\beta$-alumina porcelain acting as a partition wall and having one face kept in contact with the gas to be measured, a pair of electrodes mounted such that the $\beta$-alumina porcelain is sandwiched therebetween, and an outer circuit connected to the electrodes. In this sensor, the sodium vapor concentration is measured by detecting the ion current caused by the flow of sodium ions formed when sodium vapor contacts the $\beta$-alumina porcelain. Alternatively, the electromotive force generated by the difference in sodium vapor pressure between one side and the other side of the $\beta$-alumina porcelain is detected for measuring the sodium vapor concentration. Specifically, the difference in vapor pressure mentioned causes the sodium vapor sensor to act as a concentration cell and the electromotive force of the concentration cell is detected for measuring the sodium vapor concentration. Certainly, the sodium vapor sensor disclosed in the Japanese Patent Publication quoted above is advantageous in many respects, but leaves room for further improvement. In general, the sodium vapor introduced into the sensing system contains sodium mist. However, the sensor in question permits detecting the sodium in the form of vapor alone, failing to detect the sodium in the form of mist. It follows that it is impossible to detect the total amount of sodium contained in the gas under examination.

The difficulty mentioned above may be overcome by providing the sensor with a means for heating the $\beta$-alumina porcelain to a temperature high enough to vaporize the sodium mist. Certainly, the sensor provided with such a heating means permits detecting all the sodium contained in the gas at high accuracy, but difficulties reside in the field of application of the sensor itself. For example, it is difficult to mount a sensor directly to such large equipment as a pressure vessel of a fast breeder because great restrictions are given by the location, shape, etc. of the portion at which the sensor is mounted. Further, it is difficult to mount the sensor directly to a vessel housing a pressurized hot gas in view of the resistances of the sensor to pressure and heat.

SUMMARY OF THE INVENTION

An object of this invention is to provide a unit for measuring the alkali metal vapor concentration of a gaseous phase satisfying the requirements of a measuring device, easy to mount, handle and operate, and capable of performing the measuring function on the basis of an on-line system.

According to this invention, there is provided a unit for measuring the alkali metal vapor concentration of a gaseous phase, comprising a gas inlet pipe, a container provided with a heating means for vaporizing the alkali metal mist contained in the gas, and a $\beta$-alumina sensor serving to measure the alkali metal vapor concentration,
- a vapor trap connected to the container via a gas conduit and serving to condense and remove the alkali metal vapor contained in the gas,
- a gas pump having the suction port connected to the vapor trap via a gas conduit, and
- a gas discharge pipe connected to the discharge port of the gas pump.

DETAILED DESCRIPTION OF THE PREFERRED EMBODIMENT

Figure 1:
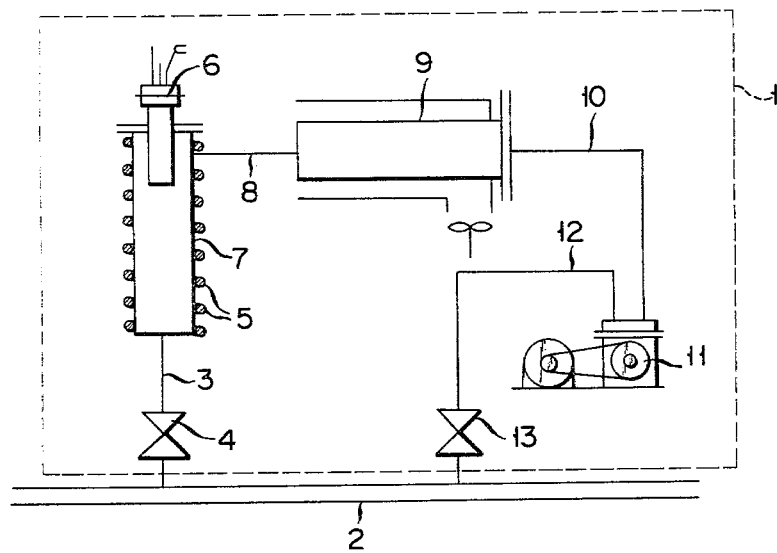
FIG. 1 shows a unit for measuring the alkali metal vapor concentration of a gaseous phase according to one embodiment of this invention.

It is seen from FIG. 1 that a unit 1 for measuring the alkali metal vapor concentration of a gaseous phase is mounted to a cover gas pipe 2 of a fast breeder. A cover gas such as Ar or He, which contains sodium vapor, flows through the cover gas pipe 2. As shown in the drawing, the unit 1 comprises, a container 7, a vapor trap 9 and a gas pump 11. The container 7 is provided with a heater 5 and an alkali metal vapor measuring sensor 6 utilizing a β-alumina porcelain as the electrolyte and is connected to the cover gas pipe 2 via a pipe 3 and a valve 4. Further the container 7 is connected to the vapor trap 9 via a pipe 8, and the vapor trap 9 to the gas pump 11 via a pipe 10. Still further, the gas pump 11 is connected to the cover gas pipe 2 via a pipe 12 and a valve 13. The sensor 6 comprises a temperature measuring means like a thermocouple, a temperature control circuit, etc. as required.

In operating the unit 1 described above, the valves 4 and 13 are opened and the gas pump 11 is operated so as to introduce the cover gas containing sodium vapor into the container 7 through the valve 4 and the pipe 3. Since the temperature within the container 7 is kept high enough by the heater 5, the sodium mist contained in the cover gas is vaporized within the container 7. It follows that the sodium content of the gas measured by the sensor 6 is free from an error caused by the presence of sodium mist. Incidentally, the heater 5, which is mounted on the outer surface of the container 7 in the embodiment of FIG. 1, may be mounted directly on the sensor 6.

The gas further flows from the container 7 to the vapor trap 9 through the pipe 8. The sodium vapor contained in the gas is condensed within and discharged from the vapor trap 9 which is provided with a cooling means utilizing air-cooling, water-cooling, or the like. It is necessary to remove the sodium vapor from the gas because the sodium vapor corrodes the gas pump 11. The gas coming from the vapor trap 9 is returned to the cover gas pipe 2 through the pipe 10, gas pump 11, pipe 12 and valve 13. Naturally, the gas pump 11 is necessary for circulating the sample gas through the unit 1 for measuring the alkali metal vapor concentration of the gas.

In the embodiment of FIG. 1, the unit 1 is mounted to the cover gas pipe 2 serving to control the pressure of a cover gas such as Ar or He. But, the unit 1, may be used in various other fashions. For example, it is possible to mount the unit 1 directly to the pressure vessel of a nuclear reactor. In this case, the unit 1 performs satisfactory functions even if the interior of the pressure vessel is maintained at a high temperature and a high pressure because the unit 1 forms its own loop separately from the pressure vessel. It should also be noted that the unit 1 may be operated alternatively on the basis of a batch system with the valves 4 and 13 kept closed.

Figure 2:
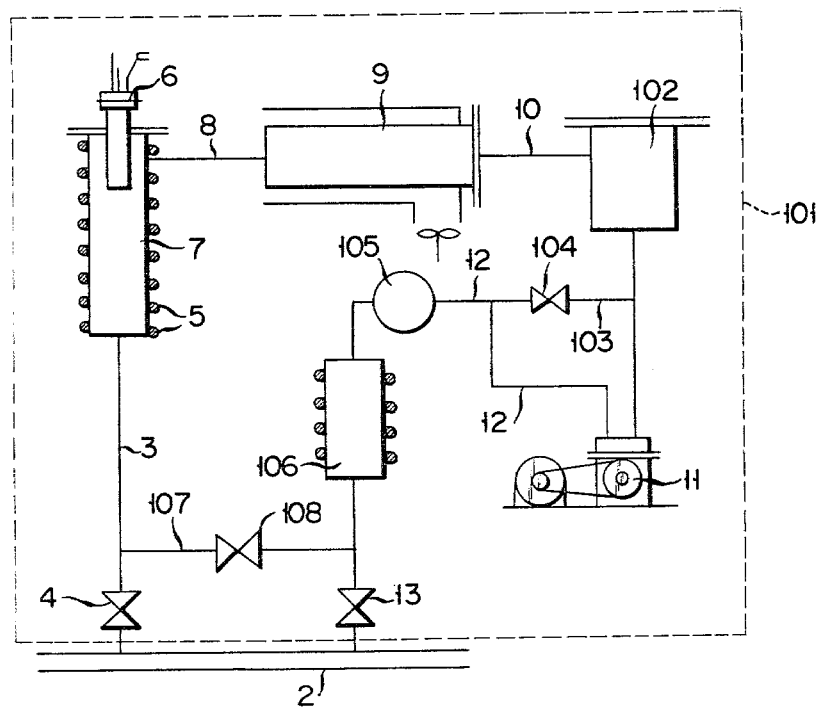
FIG. 2 shows a unit for measuring the alkali metal vapor concentration of a gaseous phase according to another embodiment of this invention.

FIG. 2 shows a unit 101 for measuring the alkali metal vapor concentration according to another embodiment of the present invention. In FIGS. 1 and 2, the same members of the unit are denoted by the same reference numerals. As readily seen by comparison with FIG. 1, the unit 101 of FIG. 2 is provided by incorporating a filter 102, a bypass pipe 103, a valve 104, a flow meter 105, a heater 106, a valve 108 and a bypass pipe 107 into the unit 1 of FIG. 1. The filter 102 mounted to the pipe 10 between the vapor trap 9 and the gas pump 11 serves to remove the sodium mist formed in the vapor trap 9. The flow meter 5 mounted to the pipe 12 serves to measure the flow speed of the gas downstream of the gas pump 11. The heater 106 serves to heat the gas returning to the cover gas pipe 2 to a level equal to the temperature of the gas flowing within the pipe 2 so as to prevent the disturbance of temperature distribution within the pipe 2 as well as thermal stress of the pipe 2. The bypass pipe 103 and the valve 104 connected between the suction and discharge sides of the gas pump 11 serve to control the flow of the gas. However, these pipe and valve are unnecessary if the gas pump 11 itself is capable of controlling the gas flow. Further, the bypass pipe 107 and the valve 108 are effective for enabling the unit 101 to start up smoothly and for conducting maintenance of the unit 101 in the event of abnormality occurrence. Specifically, the gas is circulated within the unit by opening the valve 108 with the valves 4 and 13 kept closed until the unit is rendered ready for normal operation.

The unit shown in each of FIGS. 1 and 2 is mounted to the cover gas pipe 2. In other words, the unit forms a bypass with respect to the cover gas pipe 2 and, thus, the gas subjected to the measurement of the alkali metal vapor concentration is returned to the cover gas pipe 2. However, the gas coming from the measuring unit is not necessarily returned to the cover gas pipe. The gas in question may be collected in another container or discharged into the atmosphere in some cases. Incidentally, the valves 4 and 13 are closed so as to isolate the measuring unit from the cover gas pipe during nonuse of the measuring unit.

As described above in detail, the unit of this invention necessitates making no substantial modification to the equipment or piping containing a gas which is to be measured and permits measuring the alkali metal vapor concentration of the gas on the basis of an on-line system. Further, the measured value is free from influences of the conditions such as temperature within an equipment housing the cover gas because the β-alumina sensor is not mounted directly to the equipment. Still further, the measured value is very accurate because the unit is provided with a heating means for vaporizing the sodium mist contained in the cover gas.

What we claim is:

1. A unit for measuring the alkali metal vapor concentration of a gaseous phase, serially comprising in the gas flow direction;

a gas inlet pipe connected to a source of alkali metal vapor containing gas, a container provided with a heating means for vaporizing the alkali metal mist contained in the gas, and a sensor utilizing a β-alumina porcelain as electrolyte and serving to measure the alkali metal vapor concentration, a vapor trap connected to the container via a gas conduit and serving to condense and remove the alkali metal vapor contained in the gas, a gas pump having the suction port connected to the vapor trap via a gas conduit, a gas discharge pipe connected to the discharge port of the gas pump; and a bypass pipe provided with a valve and connected between the gas inlet pipe and gas discharge pipe.

2. The unit according to claim 1, wherein each of the gas inlet pipe and the gas discharge pipe is connected via a valve to a pipe through which flows a gas containing alkali metal vapor.

3. The unit according to claim 1, wherein the heating means is a heater mounted on the outer surface of the container.

4. The unit according to claim 1, wherein the heating means is a heater mounted on the sensor.

5. The unit according to any one of claims 1 or 2 or 3 or 4, wherein a filter serving to remove the alkali metal mist formed in the vapor trap is mounted to the gas conduit between the vapor trap and the gas pump.

6. The unit according to claims 1 or 2 or 3 or 4, wherein a bypass pipe provided with a valve is connected between the suction and discharge sides of the gas pump.

7. The unit according to any one of claims 1 or 2 or 3 or 4, wherein a heater for heating the gas discharge from the unit is mounted to the gas discharge pipe.

* * * * *